United States Patent [19]

Binard et al.

[11] 4,142,525
[45] Mar. 6, 1979

[54] SYRINGE ASSEMBLY

[75] Inventors: William J. Binard; Anthony J. Ciarico, both of Cary; Leonard R. Anglada, Arlington Heights; Bhupendra C. Patel, Elgin, all of Ill.

[73] Assignee: The Kendall Company, Boston, Mass.

[21] Appl. No.: 852,379

[22] Filed: Nov. 17, 1977

Related U.S. Application Data

[60] Division of Ser. No. 776,147, Mar. 10, 1977, Pat. No. 4,074,714, which is a division of Ser. No. 702,164, Jul. 2, 1976, Pat. No. 4,030,497, which is a division of Ser. No. 627,982, Nov. 3, 1975, Pat. No. 4,000,741, which is a continuation-in-part of Ser. No. 509,757, Sep. 27, 1974, abandoned.

[51] Int. Cl.² ............................................. A61M 5/00
[52] U.S. Cl. .............................. 128/218 R; 128/349 B
[58] Field of Search ............ 128/349 B, 349 BV, 348, 128/246, 245, 241, 242, 344, 218 R

[56] References Cited

U.S. PATENT DOCUMENTS

| 3,599,620 | 8/1971 | Ballin | 128/349 B |
| 3,978,863 | 9/1976 | Fettel et al. | 128/349 B |

Primary Examiner—John D. Yasko
Attorney, Agent, or Firm—Powell L. Sprunger

[57] ABSTRACT

A syringe assembly comprising, a syringe having a chamber for retaining fluid, and a plunger having one end received in the chamber for pumping fluid out of the chamber. The syringe assembly has means for limiting the amount of pressure generated by the syringe during pumping of fluid.

6 Claims, 20 Drawing Figures

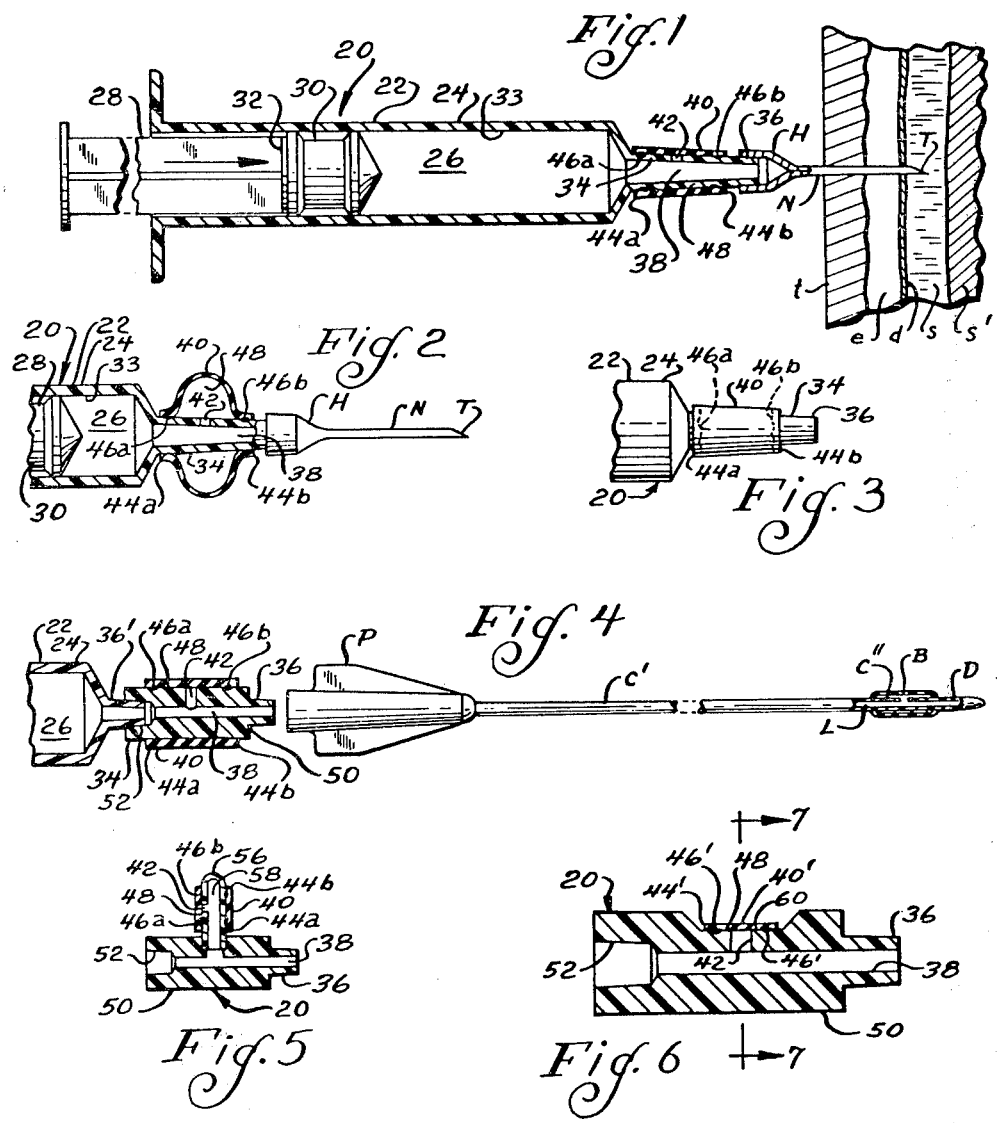
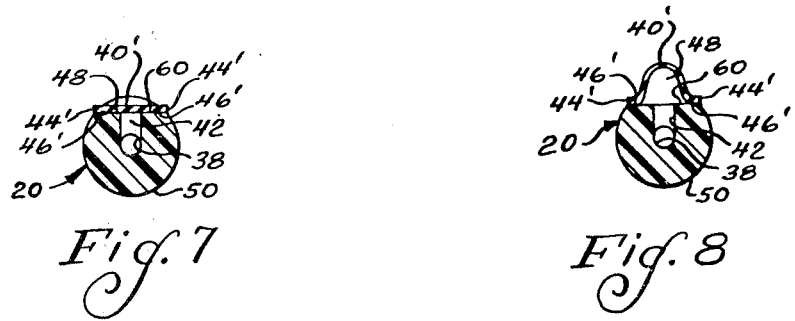

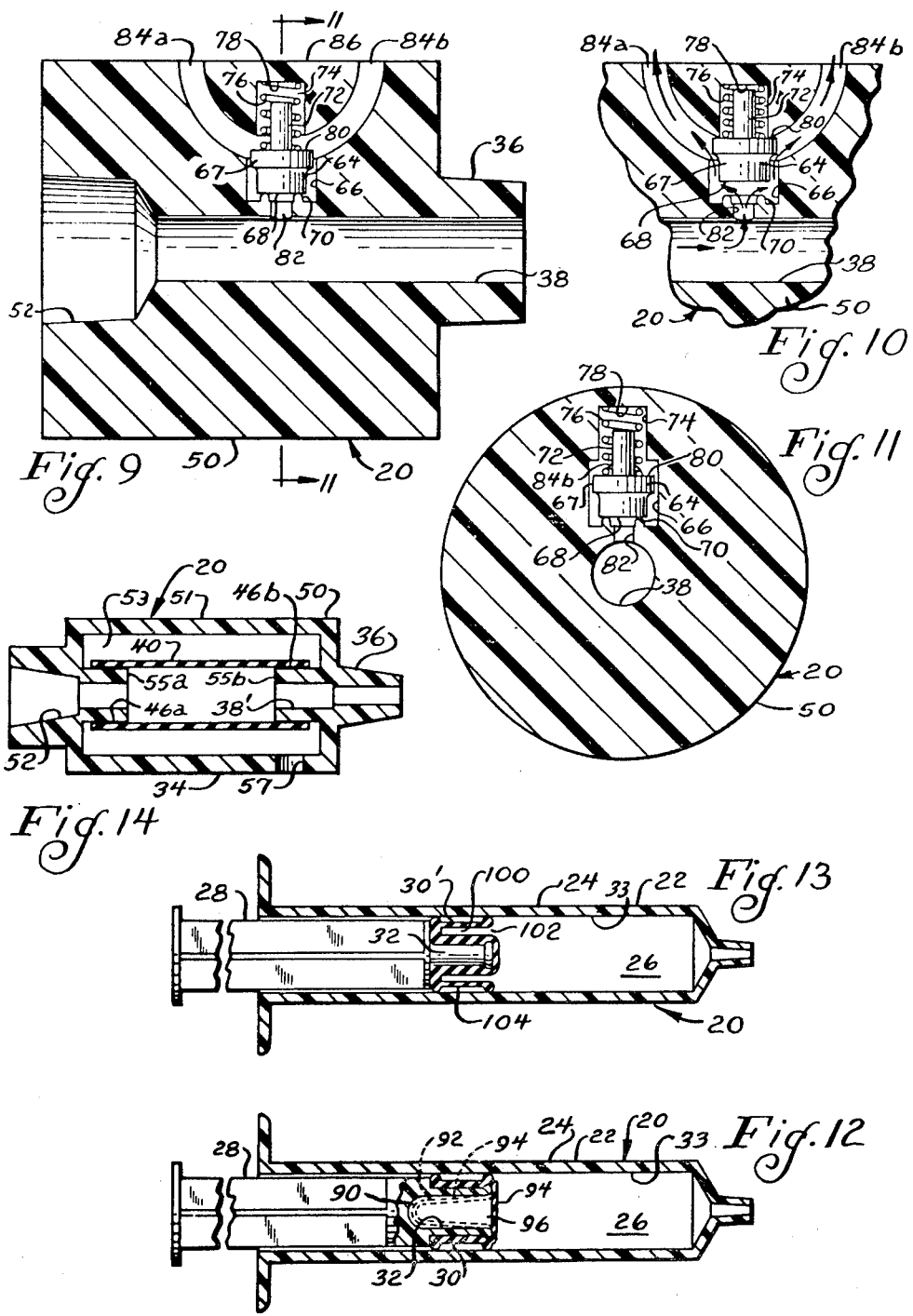

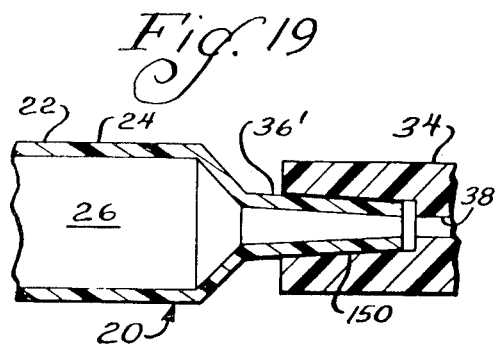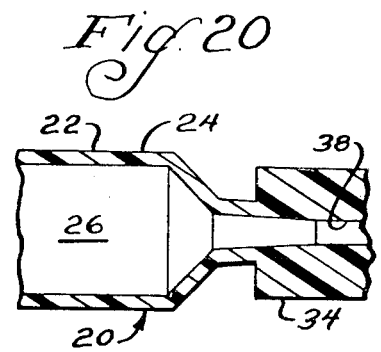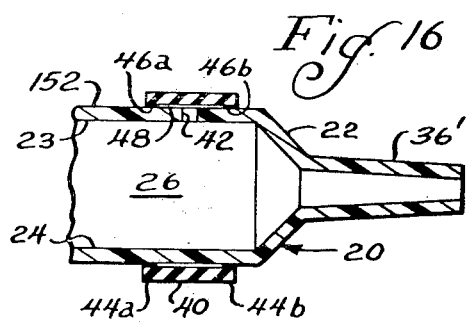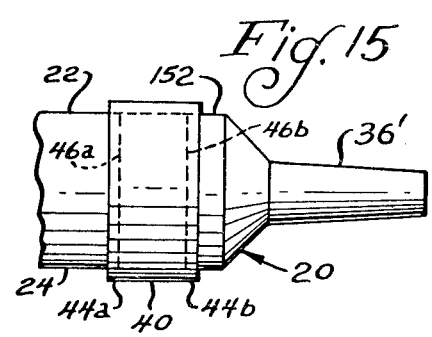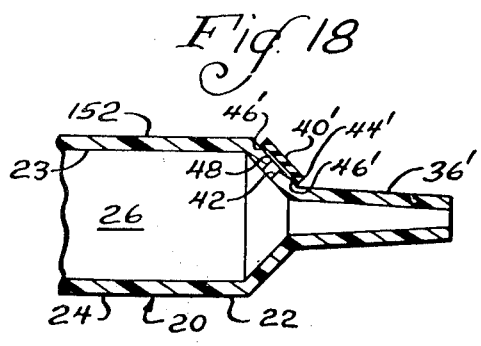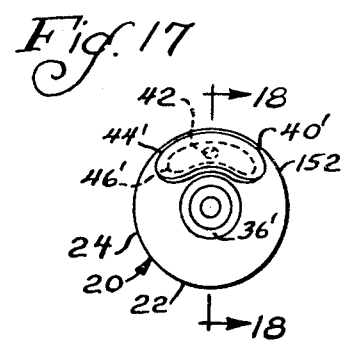

4,142,525

SYRINGE ASSEMBLY

This is a division, of application Ser. No. 776,147 filed Mar. 10, 1977 U.S. Pat. No. 4,074,714, a divisional of Ser. No. 702,164 filed July 2, 1976 U.S. Pat. No. 4,030,497, a divisional of Ser. No. 627,982 filed Nov. 3, 1975 U.S. Pat. No. 4,000,741, a continuation-in-part of Ser. No. 509,757 filed Sept. 27, 1974 now abandoned.

BACKGROUND OF THE INVENTION

The present invention relates to pumping devices, and more particularly to syringes.

Syringes are in common use today by physicians, nurses, and other hospital personnel for a variety of purposes. Frequently, syringes have been utilized to pump fluid into a body cavity of a patient or a cavity in a therapeutic device under circumstances where the pressure attained in the cavity should be limited to a predetermined value. For example, during a spinal anesthesia procedure an anesthetic solution is pumped from a syringe through a needle into the sub dural space which is essentially an inelastic pouch, and thus only a specified maximum amount of the solution should be pumped into the space as determined by the pressure in the space. Similarly, various types of cardiovascular catheters are often threaded into blood vessels, after which a balloon adjacent the distal end of the catheter is inflated through use of a syringe. If the balloon is overinflated, particularly when the catheter is placed in a smaller vessel, the vessel may be ruptured. Numerous other catheters, such as endotracheal tubes and Foley catheters, are frequently provided with retention balloons which should not be overinflated, particularly when the balloon is obstructed by a body passage.

Few of the hospital personnel realize the considerable pressures which can be generated by a hand-operated syringe. For example, a 10 c.c. syringe may readily generate pressures in the range of 50-60 lbs./sq. in., the smaller syringes being capable of developing greater pressures for the same amount of force applied to the syringe plunger. It is thus apparent that considerable care must be exercised by the user when a syringe is utilized to pump fluid into a cavity space where only a limited amount of pressure is desired. In the past, tactile sense has been used when forcing the plunger into the syringe to determine when the maximum pressure has been attained by resistance to plunger movement. Such a procedure produces speculative results, at best, in preventing harm to the patient, particularly since the syringe may readily generate relatively high pressures.

SUMMARY OF THE INVENTION

A principle feature of the present invention is the provision of a syringe assembly of simplified construction which prevents damage to a patient during use.

The syringe assembly of the present invention comprises, a syringe having a chamber for retaining fluid, and a plunger having one end received in the chamber for pumping fluid out of the chamber. The syringe assembly has means for limiting the amount of pressure generated by the syringe during pumping of fluid.

Thus, a feature of the present invention is that the syringe assembly prevents generation of an excessive amount of pressure during use to prevent possible damage to the patient.

Another feature of the invention is that the limiting means actuates at a predetermined pressure to relieve pressure in the syringe chamber.

A further feature of the invention is that the syringe assembly may provide means for indicating when the predetermined amount of pressure has been attained.

Still another feature of the invention is that in one embodiment the limiting means is associated with an extension of a syringe barrel defining the syringe chamber.

A feature of the invention is that in one embodiment the limiting means is associated with an adapter for the syringe.

Yet another feature of the invention is that in one embodiment the limiting means prevents movement of the plunger into the syringe chamber when the predetermined amount of pressure has been attained.

A further feature of the present invention is the provision of a method for performing an epidural and a spinal anesthesia procedure.

Further features will become more fully apparent in the following description of the embodiments of this invention and from the appended claims.

DESCRIPTION OF THE DRAWINGS

In the drawings:

FIG. 1 is a sectional view of one embodiment of the syringe assembly of the present invention as attached to a hollow needle;

FIG. 2 is a fragmentary sectional view of pressure limiting means in the syringe assembly of FIG. 1 as actuated above a predetermined pressure;

FIG. 3 is a fragmentary elevational view of the syringe assembly of FIG. 1;

FIG. 4 is a fragmentary sectional view of another embodiment of the syringe assembly of the present invention as being applied to a catheter;

FIG. 5 is a sectional view of an adapter in another embodiment of the syringe assembly of the present invention;

FIG. 6 is a sectional view of an adapter in another embodiment of the syringe assembly of the present invention;

FIG. 7 is a sectional view taken substantially as indicated along the line 7—7 of FIG. 6;

FIG. 8 is a sectional view of the adapter of FIG. 7 illustrating pressure limiting means as actuated above a predetermined pressure;

FIG. 9 is a sectional view of an adapter in another embodiment of the syringe assembly of the present invention;

FIG. 10 is a sectional view of the adapter of FIG. 9 illustrating valve means in the adapter as actuated above a predetermined pressure;

FIG. 11 is a sectional view taken substantially as indicated along the line 11—11 of FIG. 9;

FIG. 12 is a sectional view of another embodiment of a syringe assembly of the present invention;

FIG. 13 is a sectional view of another embodiment of a syringe assembly of the present invention;

FIG. 14 is a sectional view of an adapter in another embodiment of the syringe assembly of the present invention;

FIG. 15 is a fragmentary elevational view of another embodiment of a syringe assembly of the present invention;

FIG. 16 is a fragmentary sectional view of the syringe assembly of FIG. 15;

FIG. 17 is a front plan view of another embodiment of a syringe assembly of the present invention;

FIG. 18 is a fragmentary sectional view taken substantially as indicated along the line 18—18 of FIG. 17; and FIGS. 19 and 20 are fragmentary sectional views of additional embodiments of a syringe assembly of the present invention.

DESCRIPTION OF THE PREFERRED EMBODIMENTS

Referring now to FIGS. 1-3, there is shown a syringe assembly or syringe means generally designated 20 comprising a syringe 22. The syringe 22 has a hollow barrel 24 having a chamber 26 for retaining fluid. The syringe also has a plunger 28 having a flexible plug 30 adjacent one end 32 of the plunger received in one end of the chamber 26. The plug 30 sealingly engages against the inner surface 33 of the syringe barrel 24, with the plunger being pushed into the chamber 26 to pump fluid out of the chamber.

The syringe 22 has an extension or extension means 34 projecting from an end of the barrel 24 remote the plunger 28, with the extension 34 having a tip 36 receivable in the hub H of a hollow needle N. Of course, the tip 36 of the syringe extension 34 may be connected to any other suitable device, such as a catheter, as described below. The extension 34 has a passageway 38 which communicates with the syringe chamber 26 and the hollow needle N, when attached, and has a flexible balloon 40 which communicates with the passageway 38 through an opening 42 in the wall of the extension 34. The balloon 40 comprises a flexible sleeve which surrounds the extension 34, and has a pair of edges 44a and 44b secured to the outer surface of the extension 34 by suitable means 46a and 46b, such as adhesive. Thus, the balloon or sleeve 40 has its edges 44a and b sealed peripherally around the extension 34, such that it defines a cavity 48 intermediate the sleeve and the outer surface of the extension 34 which communicates through the opening 42 with the passageway 38.

The balloon 40 is constructed to inflate when a predetermined pressure has been reached in the passageway or chamber of the syringe, the particular pressure at which the balloon inflates being selected for the particular use contemplated for the syringe assembly. The pressure at which the balloon inflates may be controlled by a number of factors including the particular material used for the balloon, such as latex, and the thickness, durometer, and elasticity of the balloon, as well as the transverse and longitudinal radii of the balloon, according to the law of Laplace which holds that the pressure required to inflate a balloon is directionally proportional to its tangential tension and inversely proportional to its transverse and longitudinal radii.

In use of the syringe for a spinal anesthesia procedure, the chamber is filled with fluid, such as an anesthetic solution, and the syringe tip 36 is attached to the hub H of the needle N, after which the tip T of the needle may be advanced through the tissue t, the potential epidural space e, and the dura mater d of the patient's body, and inserted into the sub dural space s adjacent the spinal cord s'. The anesthetic solution is then ejected from the syringe chamber 26 into the sub dural space s by pushing the plunger 28 into the syringe chamber. Since the sub dural space is essentially an inelastic blind pouch filled with fluid, as shown in FIG. 1, and under a positive pressure, the balloon 40 of the syringe is selected to inflate at a predetermined pressure greater than the pressure in the sub dural space s. Consequently, as the solution is pumped into the sub dural space, the pressure builds up in the space until it reaches the predetermined pressure, after which the balloon 40 inflates, as shown in FIG. 2, and relieves pressure build up in the space, thus preventing harm to the patient. Accordingly, the balloon 40 serves to limit the amount of pressure generated by the syringe, and prevents ejection of further fluid into the needle N and sub dural space after the predetermined pressure has been attained. The inflated balloon also serves as an indication to the user that the predetermined amount of pressure in the space or cavity has been reached, and that the plunger should not be pushed further into the syringe chamber 26.

Another embodiment of the syringe assembly 20 of the present invention is illustrated in FIG. 4, in which like reference numerals designate like parts. In this embodiment, the extension means 34 includes an adapter 50. If desired, a conventional syringe 22 may be used having a standard luer tip 36'. The adapter 50 has a tip 36 adjacent one end for connection to a catheter C', or other suitable device, such as the needle N, and a recess 52 adjacent the other end of the adapter for attachment to the tip 36' of the syringe 22. A passageway 38 extends longitudinally through the adapter 50, and communicates between the syringe chamber 26 and the catheter C' when the ends of the adapter are connected to the syringe and catheter. The adapter 50 has a flexible sleeve or balloon 40 extending around the adapter and having its ends 44a and b secured peripherally around the outer surface of the adapter by suitable means 46a and b, such as adhesive. The sleeve 40 defines a cavity 48 intermediate the sleeve and the outer surface of the adapter 50 which communicates with the passageway 38 through the opening 42.

In use, after the syringe has been filled with fluid, the adapter 50 is attached to the tip 36' of the syringe 22, and the tip 36 of the adapter 50 is attached to the catheter C'. The catheter may be of a type having a lumen L which communicates between a proximal end P of the catheter and a cavity C" underlying a balloon B adjacent a distal end D of the catheter. For a cardiovascular catheter, as shown, the catheter is previously threaded through a vessel, and the balloon B is inflated through the lumen L by pumping fluid from the syringe chamber 26. When the partially inflated balloon B becomes obstructed by the wall of the vessel, and a predetermined amount of pressure is developed in the cavity C" defined by the balloon B, the flexible sleeve 40 inflates to limit the amount of pressure generated by the syringe and prevent overinflation of the balloon B, which otherwise might rupture the vessel.

It is apparent that the pressure limiting or indicating means associated with the syringe assembly of the present invention may be incorporated directly onto the syringe itself, as previously described, or may be placed on the adapter which is connected to the syringe. In either case, the device operates in a similar manner to prevent harm to the patient. Thus, for purposes of previous and future discussion, it is immaterial whether the limiting or indicating means is associated with the adapter or the syringe itself in the syringe assembly, with the exception of the devices described in connection with FIGS. 12 and 13.

Another embodiment of the adapter 50 in the syringe assembly 20 is illustrated in FIG. 5, in which like reference numerals designate like parts. In this embodiment, the adapter 50 includes an outwardly extending thumb 56 having a channel 58 communicating with the passageway 38. The adapter 50 has a flexible sleeve 40 extending peripherally around the thumb 56 and having its edges 44a and b secured peripherally around the thumb by means 46a and b, such as adhesive, thus defining a cavity 48 communicating with the channel 58 and passageway 38 through the opening 42. The sleeve or balloon 40 inflates, as previously described in connection with the syringe assembly of FIGS. 1–4, to limit the amount of pressure generated in the passageway 38 and the syringe chamber.

A further embodiment of the adapter 50 in the syringe assembly 20 of the present invention is illustrated in FIGS. 6–8, in which like reference numerals designate like parts. In this embodiment, a balloon 40' has its peripheral edges 44' sealed by suitable means 46', such as adhesive, to an outer surface 60 of the adapter 50 to define the cavity 48, which communicates with the passageway through the opening 42. As shown in FIG. 8, the balloon 40' inflates at a predetermined pressure, as previously described, to limit the amount of pressure generated by the syringe assembly.

Another embodiment of the adapter 50 in the syringe assembly 20 of the present invention is illustrated in FIGS. 9–11, in which like reference numerals designate like parts. In this embodiment, a valve element 64 is supported in a chamber 66, with a head 67 of the valve element 64 having a face 68 for sealing against a seat 70 in the chamber 66. The head 67 has a stem 72 extending from an end of the head remote the face 68, with the stem 72 being received in a cavity 74 in the adapter 50. A helical spring 76 surrounds the stems 72 and extends between a back surface 78 of the cavity 74 and a back surface 80 of the head 67. The adapter 50 has a channel 82 communicating between the passageway 38 and the chamber 66 adjacent the seat 70, and a pair of channels 84a and 84b communicating between the chamber 66 and an outer surface 86 of the adapter 50. As illustrated in FIG. 9, the spring 76 biases the head 67 of the valve element to a first position with the face 68 sealing against the seat 70 to prevent passage of fluid from the channel 82 into the chamber 66. However, when a predetermined amount of pressure is reached in the passageway 38, the spring 74 permits movement of the valve element to a second position with the face 68 of the head 67 spaced from the seat 70, as shown in FIG. 10, and fluid then passes from the passageway 38 through the channel 82, chamber 66, and the channels 84a and b to the outer surface 86 of the adapter 50, as indicated by the direction of the arrows in the drawing. Thus, the valve means is actuated at a predetermined pressure to relieve pressure in the passageway 38, and limit the amount of pressure generated by the syringe assembly. The pressure at which the valve means is actuated may be selected by the particular structure of the valve assembly, such as the particular helical spring 74 utilized in the adapter 50.

Another embodiment of the syringe assembly 20 of the present invention is illustrated in FIG. 14, in which like reference numerals designate like parts. In this embodiment, the adapter 50 has an outer transparent cylindrical shield 51 defining a chamber 53, and a pair of extensions 55a and 55b extending into the chamber 53 and partially defining the passageway 38'. The tubular sleeve 40 has its ends received on the extensions 55a and b and secured in place by suitable means 46a and b, such as adhesive. The sleeve 40 expands to limit the amount of pressure generated by the syringe assembly, as previously described, and is visible to the user through the transparent shield to determine when the sleeve has expanded. The shield serves to protect the sleeve, and air is permitted to pass from the chamber 53 through a vent 57 in the shield to permit expansion of the sleeve.

Another embodiment of the syringe assembly 20 of the present invention is illustrated in FIGS. 15 and 16, in which like reference numerals designate like parts. In this embodiment, the flexible balloon or sleeve 40 extends around the syringe barrel 24. The sleeve 40 is secured to an outer surface 152 of the syringe 22 by suitable means 46a and b, such as adhesive, adjacent the edges 44a and b of the sleeve 40, in order to define a cavity 48 intermediate the sleeve 40 and barrel 24 which communicates with the syringe chamber 26 through an opening 42 in the barrel 24. The sleeve 40 inflates above a predetermined pressure, as previously described, to limit the amount of pressure generated by the syringe.

Another embodiment of the syringe assembly of the present invention is illustrated in FIGS. 17 and 18, in which like reference numerals designate like parts. In this embodiment, a balloon 40' has its peripheral edges 44' sealed by suitable means 46', such as adhesive, to the outer surface 152 of the syringe 22 to define the cavity 48, which communicates with the chamber 26 through the opening 42. The balloon 40' inflates at a predetermined pressure, as previously described to limit the amount of pressure generated by the syringe.

Another embodiment of the syringe assembly 20 of the present invention is illustrated in FIG. 19, in which like reference numerals designate like parts. In this embodiment, the extensions 34 described in connection with FIGS. 4–14 may be permanently affixed to the syringe tip 36' by suitable means 150, such as adhesive. As shown in FIG. 20, the extensions 34 may be constructed as an integral part of the syringe 22, if desired.

Another embodiment of the syringe assembly of the present invention is illustrated in FIG. 12, in which like reference numerals designate like parts. In this embodiment, the barrel 24 of the syringe 22 is transparent, and the plunger 28 has a flexible plug 30 adjacent the one plunger end 32 which is received in the syringe chamber 26. The one end 32 of the plunger 28 includes a centrally located transparent member 90 having a cavity 92 facing the syringe chamber 26, with the transparent member 90 being visible through the barrel 24. A flexible diaphragm 94 is supported by the plug 30 and extends across an opening 96 intermediate the cavity 92 in the transparent member 90 and the syringe chamber 26. When a predetermined pressure has been attained in the syringe chamber 26, the diaphragm 94 flexes from a first position adjacent the opening 96, as shown by solid lines in the drawing, to a second position received in the transparent member 90, as shown by dotted lines in the drawing. The diaphragm 94 is thus visible to the user in its second position and serves as an indication that the predetermined amount of pressure has been reached in the syringe chamber, and that the user should cease pumping the syringe.

A further embodiment of the syringe assembly of the present invention is illustrated in FIG. 13, in which like reference numerals designate like parts. In this embodiment, the plunger 28 has a flexible plug 30' adjacent the one plunger end 32 which seals against the inner surface 33 of the barrel 24. The plug 30' has an annular slot 100 having one end 102 communicating with the syringe cavity 26, and defining an annular flexible side wall 104 of the plug 30' adjacent the inner surface 33 of the syringe barrel 24. The side wall 104 of the plug 30' flexes responsive to a predetermined pressure in the syringe chamber 26, and engages against the inner surface 33 of the syringe barrel 24 to impede movement of the plunger into the syringe chamber. Thus, when the predetermined amount of pressure is generated by the syringe, resistance to movement of the syringe plunger 28 into the syringe barrel 24 becomes noticeable to the user, and movement of the plunger is then stopped to prevent damage to the patient.

Thus, there has been described a syringe assembly which has means for limiting the amount of pressure generated by the syringe assembly to prevent harm to a patient. In addition, the syringe assembly indicates to the user when the predetermined amount of pressure has been reached.

According to the present invention, methods are also provided for performing an epidural and a spinal anesthesia procedure. In a spinal anesthesia procedure, the tip of a needle, used to perform the procedure, is advanced through the body tissue t, the epidural space e, which is at a slight negative pressure, and the dura mater d into the sub dural space s, which is at a positive pressure, as previously described in connection with FIG. 1. According to a method of the present invention, a balloon of the adapter in the syringe assembly is selected to inflate at a first predetermined pressure less than the pressure in the sub dural space, and a balloon on the syringe, which is removably attached to the adapter, is selected to inflate at a second predetermined pressure greater than the pressure in the sub dural space. When the needle tip T pierces the dura mater d and enters the sub dural space s, fluid in the space actuates the balloon on the adapter due to the higher pressure in the space relative the first predetermined pressure, thus indicating that the needle tip is at the proper location in the space for performing the spinal anesthesia procedure. The adapter may be removed from the needle and syringe, and the syringe is attached to the needle to eject anesthetic solution into the sub dural space. The balloon on the syringe limits the amount of pressure generated by the syringe to prevent harm to the patient, as previously described.

Alternatively, first and second adapters may be used in conjunction with a standard syringe, the first adapter having a balloon inflatable at the first predetermined pressure, and the second adapter having a balloon inflatable at the second predetermined pressure. The balloon of the first adapter is utilized to determine when the needle tip is located in the sub dural space, after which the first adapter is replaced with the second adapter for pumping the anesthetic solution into the space.

A method is also provided for performing an epidural anesthesia procedure with the syringe assembly of the present invention. After the tip of a needle, attached to a syringe or an adapter and syringe, is advanced into the body tissue, the syringe plunger is pushed sufficiently into the syringe chamber to inflate a balloon on the syringe assembly with anesthetic solution from the chamber. The needle tip is then advanced toward the epidural space. When the needle tip enters the epidural space the solution from the syringe assembly flows into the space due to the pressure generated by the inflated balloon relative the negative pressure in the space. Thus, the balloon deflates and indicates to the user that the needle tip is properly located for performing the procedure. The anesthetic solution may then be ejected from the syringe into the epidural space. Accordingly, the method of the invention prevents the user from improperly puncturing the dura mater during the epidural anesthesia procedure.

The foregoing detailed description is given for clearness of understanding only, and no unnecessary limitations should be understood therefrom, as modifications will be obvious to those skilled in the art.

We claim:

1. A syringe, comprising:
   a barrel having a chamber for retaining fluid;
   a body member extending from said barrel and defining a tip for attachment to a fluid receiving device, said body member having a shield defining a chamber of fixed volume; and
   a flexible sleeve in said chamber having ends secured to the body member with the sleeve communicating between said tip and the chamber, said sleeve being inflatable at a predetermined pressure to relieve pressure generated by the syringe.

2. An adapter for a syringe and a fluid receiving device, comprising:
   a body member having a shield defining a chamber of fixed volume, first means for releasably attaching the body member to the syringe, second means for releasably attaching the body member to the receiving device, and passageway means in the first and second attaching means communicating with the syringe and receiving device when the body member is connected therebetween; and
   a flexible sleeve in said chamber having ends secured to the body member with the sleeve being in communication with said passageway means, said sleeve being inflatable at a predetermined pressure to relieve pressure in the passageway means.

3. The adapter of claim 2 wherein said shield is transparent.

4. The adapter of claim 2 wherein said shield at least partially surrounds said sleeve.

5. The adapter of claim 2 wherein said body member includes first and second spaced extensions extending into said chamber, and in which ends of said sleeve are secured to said extensions.

6. The adapter of claim 2 wherein said shield includes opening means for venting the chamber to the atmosphere.

* * * * *